United States Patent
Campbell et al.

(10) Patent No.: US 7,262,038 B2
(45) Date of Patent: Aug. 28, 2007

(54) SIMPLIFIED EUKARYOTIC NITRATE REDUCTASE

(75) Inventors: Wilbur H Campbell, Lake Linden, MI (US); Guillaume G Barbier, East Lansing, MI (US); Ellen R Campbell, Lake Linden, MI (US)

(73) Assignee: Nitrate Elimination Co., Inc., Linden, MI (US)

( * ) Notice: Subject to any disclaimer, the term of this patent is extended or adjusted under 35 U.S.C. 154(b) by 355 days.

(21) Appl. No.: 10/498,697

(22) PCT Filed: Dec. 10, 2002

(86) PCT No.: PCT/US02/39341

§ 371 (c)(1), (2), (4) Date: Jun. 14, 2004

(87) PCT Pub. No.: WO03/052063

PCT Pub. Date: Jun. 26, 2003

(65) Prior Publication Data

US 2006/0211084 A1    Sep. 21, 2006

Related U.S. Application Data

(60) Provisional application No. 60/340,237, filed on Dec. 14, 2001.

(51) Int. Cl.
| | |
|---|---|
| *C12N 9/06* | (2006.01) |
| *C12N 1/19* | (2006.01) |
| *C12N 1/21* | (2006.01) |
| *C12N 15/63* | (2006.01) |
| *C07H 21/04* | (2006.01) |

(52) U.S. Cl. ............... 435/191; 435/252.3; 435/254.11; 435/254.22; 435/320.1; 536/23.2

(58) Field of Classification Search .................. None
See application file for complete search history.

(56) References Cited

U.S. PATENT DOCUMENTS 5,612,198 A    3/1997    Brierley et al. ............ 438/69.9

OTHER PUBLICATIONS

International Search Report, PCT/US02/39341, Jul. 11, 2003, 4 pgs, ISA/US.
Cloning and Disruption of the YNR1 Gene Encoding the Nitrate Reductase Apoenzyme of the Yeast Hansenula, Avila et al., FEBS Letters 366, 1995, pp. 137-142.
Nitrate and Nitrate Control of Respiratory Nitrate Reduction in Denitrifying Pseudomonas Stutzeri by a Two-Component Regulatory System Homologous to NarXL of *Escherichia coli*, Härtig et al., Journal of Bacteriology, vol. 181, No. 12, Jun. 1999, pp. 3658-2665.

*Primary Examiner*—Elizabeth Slobodyansky
(74) *Attorney, Agent, or Firm*—Fish & Associates, PC

(57) ABSTRACT

The invention provides modification to the polynucleotide coding sequence for *Pichia angusta* NAD (P)H: nitrate reductase [YNaR1; GenBank accession number Z49110], which has Enzyme Commission number 1.7.1.2 (formerly EC 1.6.6.2), yielding the polynucleotide coding sequence for simplified eukaryotic nitrate reductase (S-NaR1). The invention also provides a method for recombinant expression of said polynucleotide code in the cells of the methylotrophic yeast *Pichia pastoris* to produce the polypeptide for S-NaR1, which binds the host-produced molybdenum-molybdopterin cofactor and intracellularly forms catalytically active, nitrate-reducing enzyme as small and stable multimeric proteins. The invention also provides a method for rapid and high-yielding purification of S-NaR1 by utilizing the hexa-histidine sequence at the carboxyl-terminus of said polypeptide for immobilized metal affinity chromatography.

21 Claims, 7 Drawing Sheets

Figure 1 – SEQ ID NO. 1

| | |
|---|---|
| MetAspSerIleValThrGluValThrTyrGlyLeuGluIleLys | 15 |
| LysIleLysAspIleThrGluLeuProPheProValArgGlnAsp | 30 |
| SerProLeuThrGluValLeuProThrAspLeuLysThrLysAsp | 45 |
| AsnPheValAlaArgAspProAspLeuLeuArgLeuThrGlySer | 60 |
| HisProPheAsnSerGluProProLeuThrLysLeuTyrAspSer | 75 |
| GlyPheLeuThrProValSerLeuHisPheValArgAsnHisGly | 90 |
| ProValProTyrValProAspGluAsnIleLeuAspTrpGluVal | 105 |
| SerIleGluGlyMetValGluThrProTyrLysIleLysLeuSer | 120 |
| AspIleMetGluGlnPheAspIleTyrSerThrProValThrMet | 135 |
| ValCysAlaGlyAsnArgArgLysGluGlnAsnMetValLysLys | 150 |
| GlyAlaGlyPheAsnTrpGlyAlaAlaGlyThrSerThrSerLeu | 165 |
| TrpThrGlyCysMetLeuGlyAspValIleGlyLysAlaArgPro | 180 |
| SerLysArgAlaArgPheValTrpMetGluGlyAlaAspAsnPro | 195 |
| AlaAsnGlyAlaTyrArgThrCysIleArgLeuSerTrpCysMet | 210 |
| AspProGluArgCysIleMetIleAlaTyrGlnGlnAsnGlyGlu | 225 |
| TrpLeuHisProAspHisGlyLysProLeuArgValValIlePro | 240 |
| GlyValIleGlyGlyArgSerValLysTrpLeuLysLysLeuVal | 255 |
| ValSerAspArgProSerGluAsnTrpTyrHisTyrPheAspAsn | 270 |
| ArgValLeuProThrMetValThrProGluMetAlaLysSerAsp | 285 |
| AspArgTrpTrpLysAspGluArgTyrAlaIleTyrAspLeuAsn | 300 |
| LeuGlnThrIleIleCysLysProGluAsnGlnGlnValIleLys | 315 |
| IleSerGluAspGluTyrGluIleAlaGlyPheGlyTyrAsnGly | 330 |
| GlyGlyValArgIleGlyArgIleGluValSerLeuAspLysGly | 345 |
| LysSerTrpLysLeuAlaAspIleAspTyrProGluAspArgTyr | 360 |
| ArgGluAlaGlyTyrPheArgLeuPheGlyGlyLeuValAsnVal | 375 |
| CysAspArgMetSerCysLeuCysTrpCysPheTrpLysLeuLys | 390 |
| ValProLeuSerGluLeuAlaArgSerLysAspIleLeuIleArg | 405 |
| GlyMetAspGluArgMetMetValGlnProArgThrMetTyrTrp | 420 |
| AsnValThrSerMetLeuAsnAsnTrpTrpTyrArgValAlaIle | 435 |
| IleArgGluGlyGluSerLeuArgPheGluHisProValValAla | 450 |
| AsnLysProGlyGlyTrpMetAspArgValLysAlaGluGlyGly | 465 |
| AspIleLeuGluGlnLysLeuIleSerGluGluAspLeuAsnSer | 480 |
| AlaValAspHisHisHisHisHisHis | 489 |

Figure 2 -- SEQ ID NO. 2

```
1                                                 50
ATGGATTCTATTGTCACTGAGGTAACCTATGGTCTGGAGATCAAGAAAAT

100
CAAAGATATCACGGAGCTACCTTTTCCAGTCAGGCAAGACTCTCCTCTTA

150
CCGAGGTGCTTCCAACAGATCTGAAGACCAAAGATAATTTTGTCGCTAGA

200
GATCCTGACCTTCTTAGACTCACTGGTTCACACCCATTCAATTCTGAGCC

250
GCCACTGACAAAGCTTTATGACTCGGGGTTTCTCACTCCAGTGAGTCTTC

300
ACTTTGTGAGAAACCACGGCCCCGTTCCTTACGTTCCTGATGAAAATATT

350
TTAGACTGGGAAGTTTCAATTGAAGGGATGGTTGAAACGCCTTATAAAAT

400
CAAATTGTCAGACATAATGGAGCAGTTTGATATCTATTCAACCCCCGTTA

450
CTATGGTCTGCGCTGGAAACAGAAGAAAGGAGCAGAATATGGTAAAGAAG

500
GGAGCCGGTTTCAATTGGGGAGCAGCTGGAACATCTACTTCTCTTTGGAC

650
AGGATGCATGCTTGGAGATGTAATAGGCAAGGCTAGACCATCAAAGAGAG

600
CAAGATTCGTATGGATGGAGGGTGCAGATAATCCGGCAAACGGCGCATAC

650
CGCACCTGTATCCGCTTAAGCTGGTGTATGGACCCTGAACGGTGCATCAT

700
GATCGCATACCAGCAGAACGGCGAGTGGTTGCATCCTGACCATGGAAAGC

750
CCCTTCGAGTAGTAATCCCCGGTGTTATTGGTGGACGATCAGTCAAATGG
```

Figure 2. Continued

```
                                                     800
CTAAAGAAACTAGTAGTGAGCGATCGGCCGTCTGAAAATTGGTATCATTA

850
TTTTGATAATCGGGTTCTTCCAACCATGGTGACGCCAGAGATGGCTAAAA

900
GTGACGACAGGTGGTGGAAAGACGAGCGATATGCCATATATGATCTGAAC

950
TTGCAAACGATCATTTGCAAGCCCGAAAATCAGCAGGTTATCAAGATTTC

1000
AGAGGACGAGTACGAAATTGCAGGTTTTGGCTACAACGGAGGTGGAGTCA

1050
GAATAGGCCGGATTGAGGTCAGTCTTGACAAAGGGAAGAGTTGGAAACTG

1100
GCAGATATAGACTATCCGGAAGACAGATATAGGGAAGCAGGTTACTTCAG

1150
ATTGTTTGGCGGACTTGTGAATGTTTGCGACAGAATGAGCTGCCTGTGCT

1200
GGTGTTTCTGGAAGCTCAAGGTTCCTCTTTCTGAATTAGCAAGGTCAAAA

1250
GATATTCTCATTCGTGGCATGGATGAGCGTATGATGGTTCAGCCGCGCAC

1300
GATGTACTGGAACGTAACGTCCATGCTGAACAACTGGTGGTATCGAGTCG

1350
CCATTATCCGCGAGGGTGAGAGTCTTCGATTTGAGCATCCCGTGGTGGCC

1400
AACAAGCCTGGCGGTTGGATGGATAGGGTCAAGGCAGAGGGTGGAGATAT

1450
TCTAGAACAAAAACTCATCTCAGAAGAGGATCTGAATAGCGCCGTCGACC

1470
ATCATCATCATCATTGA
```

SIMPLIFIED EUKARYOTIC NITRATE REDUCTASE

This application is a 371 of PCT/US02/39341, filed Dec. 10, 2002, which is an international application claiming the benefit of U.S. Provisional Application 60/240,237, filed Dec. 14, 2001.

FIELD OF THE INVENTION

This invention relates to a process for production of the polypeptide and bound molybdenum-molybdopterin cofactor for the nitrate-reducing portion of *Pichia angusta* NAD (P)H: nitrate reductase (simplified eukaryotic nitrate reductase or S-NaR1) with nitrate-reducing catalytic activity. The invention further relates to purification of S-NaR1 by immobilized metal affinity chromatography utilizing the hexahistidine sequence expressed at the carboxyl-terminus of the simplified eukaryotic nitrate reductase enzyme.

BACKGROUND OF THE INVENTION

Eukaryotic nitrate reductase (NaR), which catalyzes the pyridine nucleotide-dependent reduction of nitrate to nitrite, exists in nature in three forms: NADH: NaR (EC 1.7.1.1, formerly EC 1.6.6.1); NAD(P)H: NaR (EC 1.7.1.2, formerly EC 1.6.6.2); and NADPH: NaR (EC 1.7.1.3, formerly EC 1.6.6.3). These three forms of NaR are very similar in molecular composition, with the holo-enzyme containing one equivalent each of flavin adenine dinucleotide, heme-iron, and molybdenum-molybdopterin bound to an approximately 100,000 Dalton polypeptide subunit, which dimerizes to constitute the catalytically active enzyme (Redinbaugh and Campbell, 1985; Solomonson and Barber, 1990; Campbell, 1999; 2001).

Natural holo-NaR has been purified and utilized from yeasts and fungi (Fischer et al., 1992, U.S. Pat. No. 5,169,758; Johannssen et al., 1994, U.S. Pat. No. 5,294,539). Eukaryotic holo-NaR was demonstrated to work as a component of a nitrate removal bioreactor for remediation of potable water when formulated with electron-carrying dyes and bacterial denitrification enzymes (Mellor et al., 1992; U.S. Pat. No. 5,403,450). NaR has also been formulated in various types of nitrate biosensors for the detection of nitrate in water where the enzyme was "wired" to an electrode by mediating electron transfer with electron-carrying dyes, such as methyl viologen, or other electron-carrying complexes mediating electron transfer between the enzyme and the electrode of the biosensor (Glazier et al, 1998; Campbell, 1999). U.S. Pat. Nos. 5,942,388; 5,942,103; and 5,922,616). Although holo-NaR performs well in these applications, it would be desirable to produce a simplified NaR system that retains the useful nitrate-reducing properties of holo-NaR, but is smaller and less complex in structure.

Although the complete three-dimensional structure of NaR is not known, the binding sites for the 3 internally bound cofactors (namely, flavin adenine dinucleotide, heme-iron, and molybdenum-molybdopterin) have been assigned to different parts of the NaR polypeptide sequence. In the carboxyl-terminal region of the NaR polypeptide, flavin adenine nucleotide cofactor binds and the polypeptide folds to generate the pyridine nucleotide active site where electrons are donated to the enzyme by NADH or NADPH or both depending on the type of NaR. Thus, it is in this region of the enzyme where variation in structure is found for the three forms of NaR which exist in nature (Shiraishi et al., 1998). In the middle of the NaR polypeptide, the heme-iron cofactor binds to generate a cytochrome b type structure, which acts as an intermediate in catalysis to transfer electrons from the reduced flavin adenine dinucleotide to the nitrate-reducing active site. In the amino-terminal region of the NaR polypeptide, the molybdenum-molybdopterin cofactor binds and the polypeptide folds into a complex shape which constitutes the nitrate-reducing active site. Also in this amino-terminal region of the NaR polypeptide is a portion which constitutes the interface for stabilizing the dimeric structure of the enzyme that is required for catalytic activity. Thus, it appears that the dimer interface structure contributes to the formation of the nitrate-reducing active site where the molybdenum-molybdopterin is bound to the NaR polypeptide via a specific cysteine residue and other amino acid residues nearby in the molybdenum-molybdopterin binding region of the NaR polypeptide (Campbell, 1999; 2001).

The nitrate-reducing molybdenum-molybdopterin-containing amino-terminal fragment of NaR has not previously been produced in any recombinant expression system. However, other fragments of Na-R have been produced recombinantly. For example, the flavin adenine nucleotide-containing carboxyl-terminal fragment of holo-NaR, which is known as the cytochrome b reductase fragment of NaR, has been expressed in recombinant form in *Escherichia coli* and studied by site-directed mutagenesis of active site residues and pyridine nucleotide binding site residues (Hyde and Campbell, 1990; Dwivedi et al., 1994; Shiraishi et al., 1998). This carboxyl-terminal fragment of NaR catalyzes NADH-dependent ferricyanide reduction. Its three-dimensional structure has been determined by x-ray diffraction analysis (Lu et al., 1994). Likewise, the combined fragment containing both the heme-iron-containing cytochrome b structure and the flavin adenine nucleotide-containing fragment in a single polypeptide, which is called the molybdenum reductase fragment of NaR and catalyzes NAD(P)H-dependent mammalian cytochrome c reductase activity, has been recombinantly expressed in *E. coli* and *Pichia pastoris* (Campbell, 1992; Mertens, 1999; Mertens et al., 2000). Although the structure of the molybdenum reductase fragment has not been determined, a three-dimensional model was generated by combining the structures of mammalian cytochrome b and the flavin adenine nucleotide-containing cytochrome b reductase fragment of NaR (Lu et al., 1995).

The functionality for enzymatic nitrate reduction of the nitrate-reducing molybdenum-molybdopterin-containing amino-terminal fragment of NaR was previously demonstrated by mild proteolytic cleavage of the holo-NaR from *Chlorella vulgaris*, which yielded a purified enzyme fragment containing the cytochrome b domain in combination with the nitrate-reducing molybdenum-molybdopterin-containing amino-terminal fragment of NaR (Solomonson and Barber, 1990).

Recombinant catalytically-active holo-NaR has been expressed in *P. pastoris* and some other systems including plants and fungi (Su et al., 1996; Su et al., 1997; Mertens, 1999; George et al., 1999; Campbell, 1999; 2001; Skipper et al., 2001). Thus, it is clear that the methylotrophic yeast, *P. pastoris*, is capable of producing a recombinant form of the complete NaR polypeptide as well as the three cofactors required for formation of the active enzyme. Furthermore, *P. pastoris* has recently been shown to produce *Pichia angusta* (formerly known as *Hansenula polymorpha*) NAD(P)H: NaR (YNaR1; EC 1.7.1.2, formerly EC 1.6.6.2) (Barbier and Campbell, 2000), which was cloned from this yeast that is closely related to *P. pastoris* (Avila et al., 1995).

Methylotrophic yeasts, such as *P. pastoris*, offer many advantages over bacteria for production of eukaryotic proteins, which include the ability to produce complex proteins like NaR and its catalytically active fragments (Su et al., 1997; Mertens et al., 2000). The *P. pastoris* expression system, which has been described previously (see, for example, U.S. Pat. Nos. 5,166,329; 5,122,465; 5,032,516; 5,004,688; 5,002,876; 4,929,555; 4,895,800; 4,885,242; 4,882,279; 4,879,231; 4,857,467; 4,855,231; 4,837,148; 4,818,700; 4,812,405; 4,808,537; and 4,683,293, the disclosures of which are hereby incorporated by reference), has been used to produce a number of recombinant proteins including the pharmaceutical insulin-like growth factor-1 (Brierley et al. 1994; U.S. Pat. No. 5,324,639), pertactin antigen (Clare et al., 2001; U.S. Pat. No. 6,197,548) and enzymes (Payne et al., 1998). In some cases, the protein of interest is produced by secretion into the media as was done for pharmaceutical insulin-like growth factor-1. However, NaR is not secreted into the media, but rather, it is produced intracellularly as a soluble protein in the cytoplasm of the methylotrophic yeast cells (Su et al., 1997; Barbier and Campbell, 2000; Skipper et al., 2001). This requires the yeast to be extracted to obtain the soluble proteins and the NaR must be purified from the other soluble proteins to obtain the purified enzyme.

BRIEF SUMMARY OF THE INVENTION

An expression system suitable for, the production of enzymatically active simplified eukaryotic nitrate reductase (S-NaR1) molecules has been developed, along with nucleotide and peptide sequences for the S-NaR1. The S-NaR1 peptides are preferably produced in methylotrophic yeast, for example, such as *Pichia pastoris*, where the peptides bind the yeast produced molybdenum-molybdopterin cofactor, which renders the S-NaR1 peptides into catalytically active nitrate-reducing enzyme proteins. The method includes the steps for transforming an organism, preferably a methylotrophic yeast, with at least one copy of a polynucleotide sequence encoding S-NaR1 and integrating the polynucleotide sequence into the yeast genome, preferably along with polynucleotide sequence encoding a tag to aid in isolation and purification, wherein both of the polynucleotide sequences are under the control of a methanol responsive promoter region of a gene of a methylotrophic yeast. Methylotrophic yeast cells, with at least one copy of these polynucleotide sequences, efficiently produce the S-NaR1 polypeptides and incorporate the molybdenum-molybdopterin cofactor into the polypeptides to yield catalytically active enzyme proteins. The method can be scaled up from shake-flasks to fermenters for production of large quantities of S-NaR1. Scaling up to the fermenter level can be done without making major changes to the growth media and conditions.

In accordance with another embodiment of the present invention, there is provided an expression vector containing at least one copy of an expression cassette as described hereinabove.

According to another aspect of the present invention, there are provided novel methylotrophic yeast cells containing in their genome at least one copy of the above described polynucleotide fragment.

The present invention is directed to the above aspects and all associated methods and means for accomplishing such. For example, the invention includes the technology required for suitable growth of the methylotrophic yeast host cells, fermentation, and isolation and purification of the S-NaR1 gene product with the host cell produced molybdenum-molybdopterin cofactor incorporated.

BRIEF DESCRIPTION OF THE DRAWINGS

FIG. 1 provides an embodiment of a polypeptide sequence of simplified eukaryotic nitrate reductase with a poly-histidine sequence at the carboxyl-terminus.

FIG. 2 provides one embodiment of a polynucleotide sequence of simplified eukaryotic nitrate reductase.

DETAILED DESCRIPTION OF THE INVENTION

In one embodiment, there is provided a polynucleotide sequence containing at least one copy of an expression cassette containing, in the reading frame direction of transcription, the following DNA sequences:
(i) a promoter region of a methanol responsive gene of a methylotrophic yeast,
(ii) a polynucleotide sequence encoding a simplified eukaryotic S-NaR1 polypeptide such as provided in FIG. 1 (SEQ ID NO. 1), and
(iii) a transcription terminator functional in methylotrophic yeast, wherein the polynucleotide sequences are operationally associated with one another for transcription of the sequences encoding the polypeptide.

In a preferred embodiment, S-NaR1 has been designed with a tag sequence to aid in the purification of the enzyme. To simply the purification of recombinant proteins, it is common practice to attach a tag sequence consisting of amino acid residues to either the amino- or carboxyl-terminus of the protein. For example, a histidine-tryptophan combination may be appended to the amino-terminus, as described for leuteinizing hormone-releasing factor (Smith et al., 1988). In another non-limiting example, a multiple histidine sequence tag may be used. In a preferred embodiment, six histidine residues are used, preferably at the carboxyl terminus. The histidine sequence is often called a "His-tag". The tags provide ligands for use in purification and can also be used as an identification label for the recombinantly expressed proteins. Tagged proteins can be purified by a number of techniques, a non-limiting example of which is immobilized metal affinity chromatography, which often employs divalent nickel, zinc, or cobalt ions as the metal for binding the protein of interest (Porath, 1992; Chaga et al., 1999). One advantage of the tagged recombinant protein is that it can be selectively purified from complex mixtures of proteins due to the low binding of endogenous proteins to the metal-chelate matrix. Often the protein of interest can be obtained as a nearly homogeneous preparation. The purification process can be carried out without denaturing the protein of interest, which is a clear advantage when working with enzymes such as S-NaR1.

Figure 3:
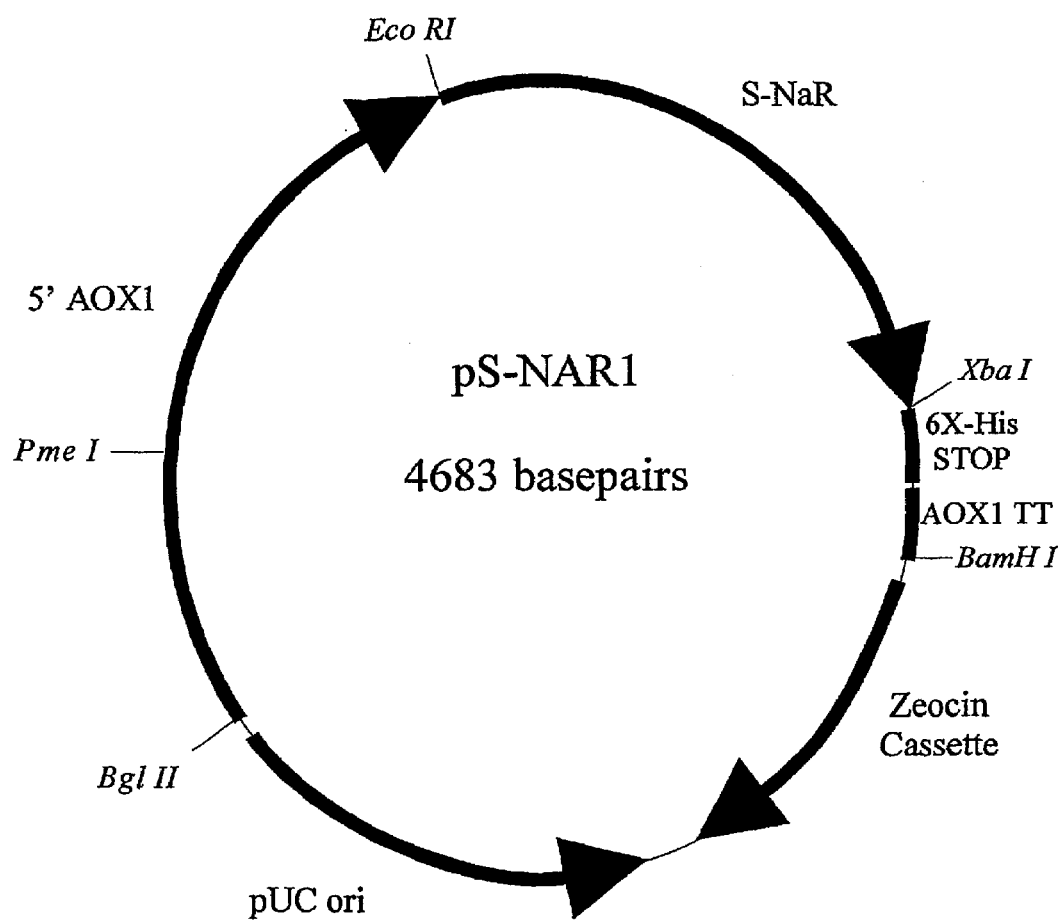
FIG. 3 provides an example of a restriction map of plasmid pS-NAR1.

In one aspect, a polynucleotide fragment containing a sequence for S-NaR1 such as, for example, illustrated in FIG. 2 (SEQ ID NO. 2), can be transformed into the genome of methylotrophic yeast cells as a linear fragment flanked by DNA sequences having homology with a target gene to integrate the fragment into the target gene, as shown in the plasmid map of FIG. 3. In this case, integration takes place without disruption of the target gene's functionality and merely incorporates the DNA fragment in tandem with the target gene, leaving both the integrated gene promoter and the target gene's promoter functional and essentially intact. Alternatively, the polynucleotide fragment can be part of a circular plasmid, which may be linearized to facilitate integration, and will integrate at a site of homology between the host genome and said DNA plasmid sequence, which may include functionality for antibiotic resistance such as to the antibiotic Zeocin™ molecule.

In another embodiment, a process is provided for producing S-NaR1 peptides and catalytically active nitrate-reducing enzyme proteins in a methylotrophic yeast host. The host-produced molybdenum-molybdopterin cofactor may be incorporated, by growing methylotrophic yeast transformants containing in their genome at least one copy of a polynucleotide sequence encoding an S-NaR1 polypeptide, as discussed above. In a preferred embodiment, the polynucleotide sequence is operably associated with DNA encoding a tag sequence at the carboxyl-terminus of the S-NaR1 polypeptide, with both under the control of a promoter region of a methanol responsive gene of the methylotrophic yeast host. Conditions are selected that permit expression of the polynucleotide sequence in the transformants and incorporation of the host-produced molybdenum-molybdopterin cofactor into the expressed polypeptide to yield catalytically active nitrate-reducing enzyme protein. Cultures of viable methylotrophic yeast cells capable of producing the catalytically active S-NaR1 and its peptide are also within the scope of the invention.

The polypeptide product with incorporated molybdenum-molybdopterin cofactor is produced intracellularly as a soluble protein in the cytoplasm of the transformants and is present at high levels of both the polypeptide and its catalytically active form. In a preferred embodiment, the polypeptide has a tag at its carboxyl-terminus to facilitate purification of the catalytically active nitrate-reducing S-NaR1. For example, the tagged polypeptide can be separated from other soluble proteins using immobilized metal affinity chromatography (IMAC) with any of several immobilized metal ions, such as nickel, zinc or cobalt.

The term "simplified eukaryotic nitrate reductase" or "S-NaR1", as used throughout the specification and in the claims, refers to a polypeptide product that exhibits catalytic activity for nitrate reduction similar to that of natural NaR forms, as measured in recognized enzymatic assays. In one embodiment, it has a sequence as given in FIG. 1 (SEQ ID NO. 1). Variants of the sequence of SEQ ID NO. 1 may also be used. For example, polypeptides deficient in one or more of the amino acids in the amino acid sequence reported in the literature for the amino-terminal fragment of naturally occurring NaR, or polypeptides containing additional amino acids or polypeptides in which one or more amino acids in the amino acid sequence of natural NaR amino-terminal fragments are replaced by other amino acids are within the scope of the present invention, as long as they exhibit functional catalytic activity of S-NaR1, e.g., by reducing nitrate to nitrite when provided with an electron donor source such as a reduced dye like reduced methyl viologen or other reduced dyes which are known to function with natural NaR forms.

The invention is intended to embrace all the natural variations of NaR with respect to their amino-terminal fragment extending from the first amino acid residue to those which encompass the molybdenum-molybdopterin binding site and fold to form the enzyme's nitrate-reducing active site when combined with the dimer interface domain and terminating at the amino acid sequence which joins the interface domain to the cytochrome b domain containing the heme-iron cofactor. Moreover, as noted above, derivatives obtained by simple modification of the amino acid sequence of naturally occurring product, e.g. by way of site-directed mutagenesis or other standard methods of modification, are included within the scope of the present invention. Forms of S-NaR1 produced by proteolysis of host cells or by proteolytic treatment of purified forms of naturally occurring NaR that exhibit similar catalytic activity to full-length S-NaR1 peptides and fully functional naturally occurring NaR or its naturally occurring amino-terminal fragment, as defined hereinabove, are also encompassed by the present invention.

The amino acids that occur in the various amino acid sequences referred to in the specification have their usual three- and one-letter abbreviations, routinely used in the art.

One embodiment of a polynucleotide (DNA) sequence encoding an S-NaR1 polypeptide is given in FIG. 2 (SEQ ID NO. 2). Variants of the polynucleotide sequence may also be used.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

According to one embodiment of the present invention, S-NaR1 peptides and catalytically active S-NaR1 enzyme proteins are produced by cells containing in their genome at least one copy of a polynucleotide sequence operably encoding the S-NaR1 peptides, preferably operably associated with a tag sequence such as a hexa-histidine tag at the carboxyl-terminus of the S-NaR1 peptides, under the control of a promoter region of a gene of the host. A number of different organisms can be used for expression of the S-NaR1 enzyme proteins. Available expression systems include prokaryotes, eukaryotes such as yeast, insect expression systems, and mammalian expression systems. Preferred systems include those capable of providing the molybdenum-molybdopterin cofactor or those that be bioengineered to provide the co-factor. These include a number of yeast genera.

Yeast species containing the biochemical pathways necessary for methanol utilization as a carbon and energy source are preferred and include, without limitation, those of the genera *Candida, Hansenula, Pichia,* and *Torulopsis,* any of which may be used in the practice of the present invention. These methylotrophic yeast species contain a number of genes responsive to methanol presence in the media and among these genes, the strongest promoter is for alcohol oxidase I (AOX1), which has been utilized for control of the expression of S-NaR1 in the present invention. A preferred host yeast species is *Pichia pastoris*. It does not produce a nitrate reductase from its own genome under natural and laboratory-culture conditions.

The operational expression cassette for S-NaR1 may be obtained by cloning the polynucleotides encoding the S-NaR1 (see FIG. 2; SEQ ID NO. 2) into an expression vector. In a preferred embodiment, the polynucleotides are cloned into the multiple cloning site of a *Pichia pastoris* expression vector. Preferred expression vectors include, without limitation, Zeocin™ *Pichia* expression vectors such as pPICZ A, B, and C, which are commercially available from Invitrogen Corp., Carlsbad, Calif.

Thus, it was possible in the present invention to produce in *P. pastoris* a simplified form of *P. angusta* NAD(P)H: NaR (S-NaR1), which contains only the amino-terminal nitrate-reducing molybdenum-molybdopterin-containing fragment of holo-NaR in a catalytically active form. To demonstrate the nitrate-reducing activity of the S-NaR1, it is necessary to use a reduced dye, such as methyl viologen, since this fragment of the enzyme does not contain the C-terminal portion of holo-NaR containing the heme-iron, flavin adenine dinucleotide and pyridine nucleotide binding sites and, consequently, can not accept electrons from NADH or NADPH. Reduced dye nitrate reductase activity is a property of holo-NaR; for example, dithionite-reduced methyl viologen, as will several other reduced dyes, supports nitrate reduction. This catalytic activity of holo-NaR is not dependent on functionality in the NADH/NADPH electron accepting active site (Campbell, 1999; 2001). Thus, the expected property of S-NaR1, namely that it functions only with reduced dyes as electron donor, has been demonstrated in the present invention.

Considering the many potential applications of NaR in the field of environmental biotechnology for nitrate monitoring and enzymatic remediation of nitrate polluted waters (Campbell, 1999), the simplified version of NaR invented here will have virtually the same applications. However, the S-NaR1 has the advantages of being smaller in size and less complex since it contains only one of the cofactors required for the complete holo-NaR. This makes S-NaR1 more suitable for many applications in environmental biotechnology than the more complex holo-NaR. In applications where the NaR catalytic activity is driven by electrons supplied by a direct current (Mellor et al., 1992; Glazier et al., 1998), either with or without electron-carrying dyes or other electron transfer mediators, S-NaR1 will work as efficiently as holo-NaR since the electrons in these systems probably bypass the heme-iron and flavin adenine dinucleotide cofactors of holo-NaR to directly reduce the nitrate-reducing active site containing the molybdenum-molybdopterin.

The invention has been described above with respect to certain preferred embodiments. Further non-limiting description is provided in the following Examples.

EXAMPLE 1

Preparation of Transformed *Pichia pastoris* Cells

*Pichia* expression vectors pPICZ were obtained from Invitrogen and used according to their instructions (pPICZ Manual, 1997), resulting in the DNA plasmid containing one copy of the S-NaR1 which was designated pS-NAR1 (see FIG. 3). In the pS-NAR1 plasmid construct, the S-NaR1 polynucleotide sequence is positioned under the control of the AOX1 promoter of *P. pastoris* and said construct also provides a Zeocin™ resistance factor permitting selection of transformants by growth on Zeocin™ containing culture media in plates or flasks (pPICZ Manual, 1997). The pS-NAR1 plasmid was made by first cloning the *P. angusta* NAD(P)H: NaR encoding polynucleotides (YNaR1; GenBank accession number Z49110) into the vector pPICZ-B using appropriate restriction endonucleases and *E. coli* as the host (Barbier and Campbell, 2000, the disclosure of which is hereby incorporated by reference). The resulting plasmid DNA was isolated, purified and restricted with XbaI restriction endonuclease. The 4.7 kilobase S-NaR1-encoding polynucleotide fragment obtained after the digestion was purified by agarose gel electrophoresis and religated by standard procedures in the art and transformed into *E. coli* and selected by Zeocin™ resistance. The pS-NAR1 plasmid which was obtained in the cloning procedure was purified and confirmed by restriction mapping on agarose electrophoresis gels. For transformation by standard practices in the art, the pS-NAR1 plasmid was restricted with PmeI to linearize it and transformed into wild-type *P. pastoris* by electroporation (*Pichia* Expression Manual, 1996; Higgins and Cregg, 1998). Transformants were selected on Zeocin™-containing plates. The Zeocin™-resistant transformants were grown in shake-flask liquid cultures to high density and the cells obtained by centrifugation and inoculated into methanol-containing media according to the standard practices in the art.

EXAMPLE 2

Preparation of Cell Extracts Containing S-NaR1

A series of S-NaR1 *P. pastoris* cell lines was grown as in Example 1 and extracted after the cells had grown in methanol media for 12 to 48 hours. The extracts were prepared by breaking the yeast cells with glass beads and centrifuging to remove the beads and cellular debris. The extracts of S-NaR1 expressing *P. pastoris* cell lines were assayed for dithionite-reduced methyl viologen NaR activity, as described in the standard literature, and found to contain from 0.44 to 0.74 units of nitrate reducing activity per milliliter of centrifuged, cellular extract (one activity unit defined as 1 micromole of nitrite produced per min).

EXAMPLE 3

Purification of S-NaR1

Figure 4:
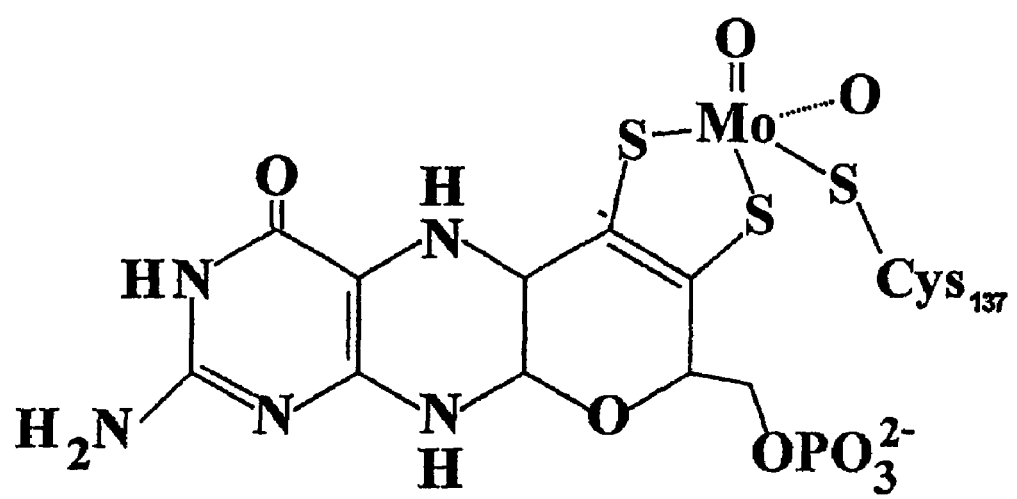
FIG. 4 provides the chemical structure of molybdenum-molybdopterin cofactor.
Figure 5:
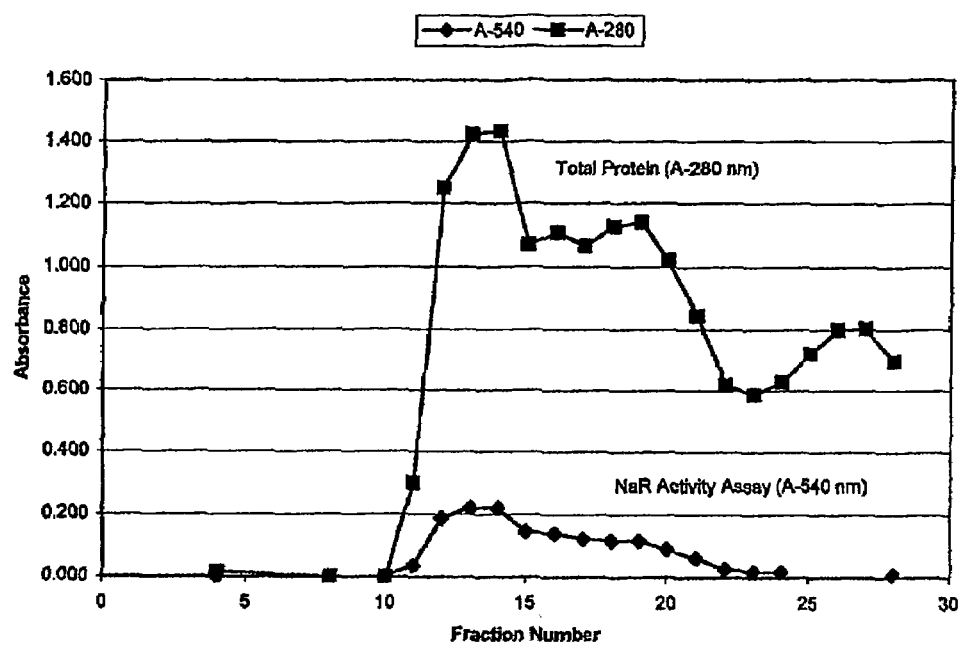
FIG. 5 provides an elution pattern of a gel-filtration column chromatograph, demonstrating the multimeric nature of simplified eukaryotic nitrate reductase.

One *P. pastoris* cell line (PICZ-S-NAR1-A1) was expressed in two 1 liter cultures in 2.8 baffled Fernbach flasks, supplemented with 0.5 millimolar sodium molybdate, and after reaching an absorbance at 600 nanometers of 10, was induced with 1% methanol for 24 hours. The S-NaR1-containing *Pichia* cells were harvested and extracted in 50 millimolar sodium phosphate, 1.5% (W/V) polyethylene glycol, pH 7.3, in a small scale glass bead mill. In this case, EDTA was omitted so that IMAC could be used to purify the S-NaR1. Centrifuged crude extract had 0.3 units NaR activity per milliliter and a specific activity of ~0.05 units per milligram protein. The centrifuged extract was applied to a 5 milliliter Nickel metal-chelate column and washed with 50 millimolar sodium phosphate, pH 7.3. Active S-NaR1 was eluted with 100 millimolar imidazole, pH 7. A fraction with 0.7 units NaR activity per milliliter and a specific activity of ~0.5 units per milligram protein (~10 fold improvement) had no distinct peaks in its visible spectrum, which indicates that no heme-iron or flavin adenine dinucleotide cofactors are present in the purified S-NaR1, as expected. Purified S-NaR1 also had no activity with NADH or NADPH as electron donor, as expected. However, since purified S-NaR1 was a catalytically active nitrate reductase with dithionite-reduced methyl viologen as electron donor, the S-NaR1 polypeptide expressed in the *P. pastoris* cells must have incorporated the molybdenum-molybdopterin cofactor (see FIG. 4) into the folds of the S-NaR1 peptides to yield the active enzyme proteins, which were purified via the hexa-histidine sequence at the carboxyl-terminus of the S-NaR1 peptides using nickel IMAC. Molecular size analysis by denaturing polyacrylamide gel electrophoresis, carried out by standard procedures in the art, revealed a protein band at ~60,000 Dalton which is near the predicted size for S-NaR1, that is 56,528 Dalton. Furthermore, using gel filtration, S-NaR1 was shown to form multimers (See FIG. 5), as expected since the construct contained the coding for the dimer interface domain of holo-NaR (Campbell, 1999; 2001). Thus, the presence of the functional dimer interface domain of NaR is established, which is known to be a critical feature of holo-NaR for production of enzyme catalytic activity.

EXAMPLE 4

Larger Scale Preparation of S-NaR1

Another *P. pastoris* cell line (PICZ-S-NAR1-A2) was expressed in fermentation culture with a 10 liter capacity fermenter (BioFlo3000, New Brunswick Scientific Co., Edison, N.J.) employing standard glycerol batch, glycerol fed batch and methanol induction conditions as normally practiced in the art (*Pichia* Expression Manual, 1996; Higgins and Cregg, 1999; Mertens et al., 2000). In this case, 2.7 kilograms of wet *Pichia* cells were obtained and the S-NaR1 activity extracted by processing in a Dyno Mill model KDL (Glen Mills, Clifton, N.J.) at a rate of 10 liter per hour with a 0.6 liter stainless steel grinding vessel filled with 500 milliliters of 0.5 millimeter glass beads and 7000 milliliters of extraction buffer consisting of 50 millimolar sodium phosphate, 0.3 molar sodium chloride, pH 7.0, 100 g glycerol per liter, while being maintained at or near four degrees centigrade, in a manner similar to that described by Mertens et al., 2000. After centrifugation to remove the cellular debris, the extract had 0.21 units of NaR activity per milliliter of extract. Thus, a total of 1445 units of S-NaR1 was produced in a single fermenter run, which represents a very high yield of enzyme protein. Purification to near electrophoretic homogeneity of the crude S-NaR1 employing TALON® metal affinity resin, as described by the manufacturer (TALON® Metal Affinity Resins User Manual, 2000) and in U.S. Pat. No. 5,962,641, the disclosure of which is incorporated by reference, yielded 477 units of NaR activity, representing 33 percent recovery of NaR activity in the crude enzyme preparation and 181 mg of purified S-NaR1 protein as estimated by the absorbance at 280 nm of the solution of purified S-NaR1 after buffer exchange into 25 millimolar MOPS (3-[N-morpholino]propanesulfonic acid, Research Organics, Cleveland Ohio.) adjusted to pH 7.0 with sodium hydroxide. This large quantity of purified S-NaR1 is easily and inexpensively utilized in many environmental biotechnology applications, which were developed employing holo-NaR for detecting, monitoring and removing nitrate from water.

EXAMPLE 5

Environmental Biotechnology Applications of S-NaR1

Holo-NaR has been used in two applications for environmental biotechnology, namely, an enzymatic nitrate removal system (Mellor et al. 1992; U.S. Pat. No. 5,403,450, the disclosures of which are hereby incorporated by reference) and various formulations of a nitrate-detecting electrode for nitrate biosensors (Heller, 1990; Glazier et al., 1998; U.S. Pat. Nos. 5,443,701; 5,942,103; 5,942,388; 5,922,616; 6,299,757, the disclosures of which are hereby incorporated by reference). In these applications, nitrate reduction is driven by direct electrical current in a "wired" system such as a co-immobilized electron-carrying dye consisting of methyl viologen, azure A, or other electron-carrying system like tethered osmium. Since these dyes directly donate electrons to the molybdenum-molybdopterin cofactor of the enzyme when the nitrate reducing activity is assayed in solution systems driven by an electron source such as sodium dithionite, it appears that the flavin adenine dinucleotide and heme-iron cofactors bound into the holo-enzyme are spectators in these dye-mediated reactions and not involved in catalysis (Campbell, 1999; 2001).

Figure 6:
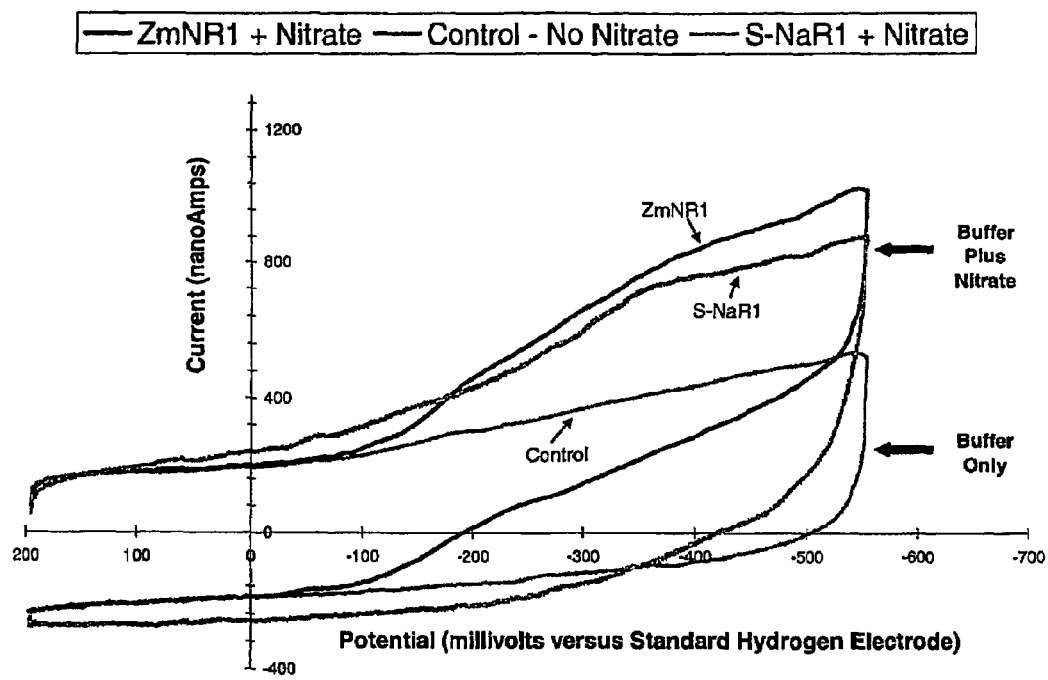
FIG. 6 provides a set of cyclic voltammograms demonstrating direct electrical current driving the catalytic nitrate-reducing activity of commercial natural corn leaf (*Zea mays*) NADH:nitrate reductase (ZmNaR1) and simplified eukaryotic nitrate reductase (S-NaR1) when formulated as protein films on commercial pyrolytic graphite electrodes.

As demonstrated herein, nitrate reduction catalyzed by S-NaR1 can be driven by dithionite-reduced methyl viologen; therefore, it can be expected that nitrate reduction catalyzed by S-NaR1 can also be driven by direct electric current mediated by either methyl viologen, its derivatives, other dyes and other forms of "wiring" the enzyme, without limitation, or in the absence of mediators. Fundamentally, the reaction is the same as the solution system, except the source of electrons is shifted from a chemical to direct electric current. To demonstrate that nitrate-reducing catalytic activity of NaR forms is driven by direct electric current in the absence of mediators, S-NaR1 and commercial natural corn leaf (*Zea mays*) NADH:nitrate reductase (The Nitrate Elimination Co., Inc., Lake Linden, Mich. 49945) were formulated as protein films on commercial pyrolytic graphite edge-plane electrodes (Pine Instrument Co., Grove City Pa.) using polymyxin B sulfate (Sigma Chemical Co., St. Louis Mo. 63195) as a promoter for film formation and MOPS (as defined herein) buffer at pH 7.0 and 22 degrees centigrade, under purified high-purity Argon gas, in a manner similar to that described by Turner et al., 1999. As shown in FIG. 6, un-mixed anaerobic solution cyclic voltammograms of the enzyme-electrode protein films, as generally carried out in the practice of the art, were used to demonstrate the control response for the enzymes in the absence of nitrate and the catalytic response in the presence of nitrate ions, which were normalized to the same control response curve to compensate for differences in experimental conditions. The increased current observed in nitrate containing solutions for S-NaR1 and commercial holo-NaR indicate the enzyme catalytic activity for nitrate reduction (FIG. 6). No increase in current is observed when nitrate ions are replaced by chloride or nitrite ions. Also when the enzyme electrode protein films are electrochemically analyzed in the presence of nitrate with added azide, a known inhibitor of the nitrate-reducing activity of holo-NaR (Campbell, 1999), no catalytic current response is found. When similar methods were used, many "reductase" enzymes displayed catalytic activity when driven by direct electric current, including bacterial nitrate reductase (Turner et al., 1999; Butt et al., 2002; Anderson et al., 2000; 2001). In summary, S-NaR1 and holo-NaR are capable of utilizing direct electric current to power catalytic nitrate reduction in a specific manner with no interference by the reaction product nitrite.

S-NaR1 of the invention substituted for holo-NaR in environmental biotechnology applications has several advantages. One advantage of S-NaR1 over holo-NaR in the environmental biotechnological applications of this enzyme is that S-NaR1 is simpler, containing only the required molybdenum-molybdopterin cofactor and a polypeptide which is one-third smaller. This means that S-NaR1 can be produced more economically and with higher efficiency in recombinant production systems. In addition, S-NaR1 is more stable than the natural holo-NaR and significantly easier to engineer by recombinant biotechnology into forms with greater utility and more robust properties, since it contains only the molybdenum-molybdopterin cofactor and has a less complex structure than holo-NaR.

The invention has been described in detail with reference to particular embodiments thereof. It will be understood, however, that variations and modifications can be effected within the spirit and scope of the invention. Variations that would occur to a person of skill in the art based on the description are within the scope of the invention, which is defined in the appended claims.

LITERATURE CITED (BIBLIOGRAPHY)

Avila, J, Perez, M D, Brito, N, Gonzalez, C, Siverio, J M (1995) Cloning and disruption of the YNR1 gene encoding the nitrate reductase apoenzyme of the yeast *Hansenula polymorpha*. FEBS Letter 366: 137-142.

Anderson, L J, Richardson, D J, Butt, J N (2000) Using direct electrochemistry to probe rate limiting events during nitrate reductase turnover. Faraday Discussions of the Chemical Society 116: 155-69.

Anderson, L J, Richardson, D J, Butt, J N (2001) Catalytic protein film voltammetry from a respiratory nitrate reductase provides evidence for complex electrochemical modulation of enzyme activity. Biochemistry 40(38): 11294-307.

Barbier, G G, Campbell, W H (2000) Expression of *Pichia angusta* nitrate reductase (YNR1) in *Pichia pastoris*. Current Topics in Gene Expression Systems: Program and Abstracts, Abstract PY 4, p. 64.

Butt, J N, Anderson, L J, Rubio, L M, Richardson, D J, Flores, E, Herrero, A (2002) Enzyme-catalyzed nitrate reduction-themes and variations as revealed by protein film voltammetry. Bioelectrochemistry 56(1-2): 17-8.

Campbell, W H (1999) Nitrate Reductase Structure, Function and Regulation: Bridging the Gap between Biochemistry and Physiology, Annual Review of Plant Physiology and Plant Molecular Biology 50:277-303.

Campbell, W H (2001) Structure and Function of Eukaryotic NAD(P)H:Nitrate Reductase. Cellular and Molecular Life Sciences. 58: 194-204.

Campbell, W H (1992) Expression in *Escherichia coli* of cytochrome c reductase activity from a maize NADH: nitrate reductase cDNA. Plant Physiology 99: 693-699.

Chaga, G, Hopp, J, Nelson, P (1999) Immobilized metal ion affinity chromatography on $Co^{2+}$-carboxymethylasparate-agraose Superflow, as demonstrated by one-step purification of lactate dehydrogenase from chicken breast muscle. Biotechnological and Applied Biochemistry 29: 19-24.

Dwivedi, U N, Shiraishi, N, Campbell, W H (1994) Identification of an "essential" cysteine of nitrate reductase via mutagenesis of its recombinant cytochrome b reductase domain. Journal of Biological Chemistry 269: 13785-13791.

George, G N, Mertens, J A, Campbell, W H (1999) Structural Changes Induced by Catalytic Turnover at the Molybdenum Site of *Arabidopsis* Nitrate Reductase. Journal of American Chemical Society, 121: 9730-31.

Glazier, S A, Campbell, E R, Campbell, W H (1998) Construction and characterization of nitrate reductase-based amperometric electrode and nitrate assay of fertilizers and drinking water. Analytic Chemistry 70: 1511-15

Heller, A (1990) Electrical Wiring of Redox Enzymes, Accounts of Chemical Research, 23(5):129-134.

Higgins, D R, Cregg, J M, eds (1998) *Pichia* Protocols, Methods in Molecular Biology series, Humana Press, Totowa, N.J.

Hyde, G E, Campbell, W H (1990) High-level expression in *Escherichia coli* of the catalytically active flavin domain of corn leaf NADH:nitrate reductase and its comparison to human NADH:cytochrome $b_5$ reductase. Biochemical and Biophysical Research Communications, 168:1285-1291.

Lu, G, Campbell, W H, Schneider, G, Lindqvist, Y (1994) Crystal structure of the FAD-containing fragment of corn nitrate reductase at 2.5 Å resolution: relationship to other flavoprotein reductases. Structure 2: 809-821.

Lu, G, Lindqvist, Y, Schneider, G, Dwivedi, U N, Campbell, W H (1995) Structural studies on corn nitrate reductase. Refined structure of the cytochrome b reductase fragment at 2.5 Å, its ADP complex and an active site mutant and modeling of the cytochrome b domain. Journal of Molecular Biology 248: 931-48

Mellor, R B, Ronnenberg, J, Campbell, W H, Diekmann, S (1992) Reduction of nitrate and nitrite in water by immobilized enzymes. Nature 355: 717-719

Mertens, J A, Shiraishi, N, Campbell, W H (2000) Recombinant Expression of Molybdenum Reductase Fragments of Plant Nitrate Reductase at High Levels in *Pichia pastoris*. Plant Physiology 123: 743-756.

Mertens, J A (1999) Expression and Biochemical Characterization of Recombinant Nitrate Reductase and Its Active Molybdenum Reductase Fragment. Ph.D. Thesis, Michigan Technological Univ., Houghton, Mich.

Payne, M S, Petrillo, K L, Gavagan, J E, DiCosimo, R, Wagner, L W, Anton, D L (1997) Engineering *Pichia pastoris* for biocatalysis: co-production of two active enzymes. Gene 194: 179-82.

*Pichia* Expression Kit: A Manual of Methods for Expression of Recombinant Proteins in *Pichia pastoris*. (1996) Invitrogen Corp., Carlsbad, Calif. 92008, Catalog no. K1710-01 (Current version L, 000126, 25-0043).

Porath, J (1992) Immobilized metal ion affinity chromatography. Protein Expression and Purification. 3 (4): 263-81.

pPICZ A, B, and C: *Pichia* expression vectors for selection on Zeocin™ and purification of recombinant proteins. (1997) Invitrogen Corp., Carlsbad, Calif. 92008, Catalog no. V190-20 (2001 version C, 000512, 25-0148).

Redinbaugh, M G, Campbell, W H (1985) Quaternary structure and composition of squash NADH:nitrate reductase. Journal of Biological Chemistry 260: 3380-3385

Shiraishi, N, Croy, C, Kaur, J, Campbell, W H (1998) Engineering of pyridine nucleotide specificity of nitrate reductase: mutagenesis of recombinant cytochrome b reductase fragment of *Neurospora crassa* NADPH:nitrate reductase. Archives of Biochemistry and Biophysics 335: 104-115

Skipper, L, Campbell, W H, Mertens, J A, Lowe, D J (2001) Pre-Steady-State Kinetic Analysis of Recombinant *Arabidopsis* NADH:Nitrate Reductase: Rate-Limiting Processes in Catalysis. Journal of Biological Chemistry 276: 26995-27002.

Smith, M C, Furman, T C, Ingolia, T D, Pidgeon, C (1988) Chelating peptide-immobilized metal ion affinity chromatography. A new concept in affinity chromatography for recombinant proteins. Journal of Biological Chemistry 263(15):7211-5.

Solomonson, L P, Barber, M J (1990) Assimilatory nitrate reductase: functional properties and regulation. Annual Review of Plant Physiology and Plant Molecular Biology 41: 225-53

Su, W, Huber, S C, Crawford, N M (1996) Identification in vitro of a post-translational regulatory site in the hinge I region of *Arabidopsis* nitrate reductase. Plant Cell 8: 519-527.

Su, W, Mertens, J A, Kanamaru, K, Campbell, W H, and Crawford N M (1997) Analysis of wild-type and mutant plant nitrate reductase expressed in the methylotrophic yeast *Pichia pastoris*. Plant Physiology 115: 1135-1143.

TALON® Metal Affinity Resins User Manual (2000) CLONTECH Laboratories Inc., Palo Alto, Calif. 94303-4230, USA, PT1320-1 (PRO3469).

Turner, K L, Doherty, M K, Heering, H A, Armstrong, F A, Reid, G A, Chapman, S K (1999) Redox properties of flavocytochrome c3 from *Shewanella frigidimarina* NCIMB400. Biochemistry 38(11): 3302-9.

---

We claim:

1. A polynucleotide containing at least one copy of an expression cassette comprising, in the reading frame direction of transcription, polynucleotide sequences comprising:
a promoter region of a methanol responsive gene of a methylotrophic yeast; a
polynucleotide sequence encoding simplified nitrate reductase (S-NaR1) polypeptide; a
transcription terminator functional in methylotrophic yeast,
wherein said polynucleotide sequences are operationally associated so that when transcribed and translated in a host, the S-NaR1 polypeptide is produced intracellularly and, after incorporation of the molybdenum-molybdopterin cofactor from the host in vivo, is catalytically active for reduction of nitrate to nitrite; and
wherein the S-NaR1 polypeptide has a sequence according to SEQ ID NO: 1, optionally truncated at amino acid 483.

2. A plasmid comprising the polynucleotide sequence of claim 1.

3. A *Pichia pastoris* yeast cell transformed with the plasmid according to claim 2.

4. The polynucleotide of claim 1, wherein the host comprises a methylotrophic yeast.

5. The polynucleotide sequence of claim 1, wherein the host comprises a methylotrophic yeast of a genus selected from the group consisting of *Candida, Hansenula, Pichia*, and *Torulopsis*.

6. The polynucleotide of claim 4, wherein said methylotrophic yeast is a strain of *Pichia pastoris*.

7. The polynucleotide of claim 5, wherein said promoter region of a methanol responsive gene of a methylotrophic yeast and the transcription terminator are derived from the *Pichia pastoris* alcohol oxidase 1 (AOX1) gene.

8. The polynucleotide sequence of claim 1, containing multiple copies of said expression cassette.

9. A *Pichia pastoris* cell transformed with the polynucleotide of claim 7.

10. A culture of viable *Pichia pastoris* cells, comprising cells of claim 9.

11. A process for producing S-NaR1 polypeptide, comprising growing *Pichia pastoris* cells of claim 9 under conditions whereby S-NaR1 is expressed intracellularly in catalytically active form after incorporating the molybdenum-molybdopterin cofactor from the host cells.

12. A recombinant polynucleotide encoding a simplified nitrate reductase, wherein the polynucleotide encodes a polypeptide consisting of the amino acid sequence set forth in SEQ ID NO: 1.

13. The polynucleotide according to claim 12, consisting of the nucleotide sequence according to SEQ ID NO. 2.

14. A recombinant DNA comprising a promoter capable of directing transcription in a yeast, operatively linked to the polynucleotide according to claim 12.

15. The DNA according to claim 14, wherein the promoter is derived from a methanol responsive gene.

16. The DNA according to claim 14, wherein the gene is an AOX-1 gene.

17. A plasmid comprising the polynucleotide according to claim 12.

18. An isolated cell transformed with the polynucleotide sequence of claim 12.

19. A culture of cells, comprising a plurality of cells according to claim 18.

20. The culture according to claim 19, wherein the cells comprise cells of a methylotrophic yeast.

21. The culture according to claim 20, wherein the cells comprise cells of *Pichia pastoris*.

* * * * *

SEQUENCE LISTING

<160> NUMBER OF SEQ ID NOS: 2

<210> SEQ ID NO 1
<211> LENGTH: 489
<212> TYPE: PRT
<213> ORGANISM: Pichia angusta

<400> SEQUENCE: 1

```
Met Asp Ser Ile Val Thr Glu Val Thr Tyr Gly Leu Glu Ile Lys Lys
1               5                   10                  15

Ile Lys Asp Ile Thr Glu Leu Pro Phe Pro Val Arg Gln Asp Ser Pro
            20                  25                  30

Leu Thr Glu Val Leu Pro Thr Asp Leu Lys Thr Lys Asp Asn Phe Val
        35                  40                  45

Ala Arg Asp Pro Asp Leu Leu Arg Leu Thr Gly Ser His Pro Phe Asn
    50                  55                  60

Ser Glu Pro Pro Leu Thr Lys Leu Tyr Asp Ser Gly Phe Leu Thr Pro
65                  70                  75                  80

Val Ser Leu His Phe Val Arg Asn His Gly Pro Val Pro Tyr Val Pro
                85                  90                  95

Asp Glu Asn Ile Leu Asp Trp Glu Val Ser Ile Glu Gly Met Val Glu
            100                 105                 110

Thr Pro Tyr Lys Ile Lys Leu Ser Asp Ile Met Glu Gln Phe Asp Ile
        115                 120                 125

Tyr Ser Thr Pro Val Thr Met Val Cys Ala Gly Asn Arg Arg Lys Glu
    130                 135                 140

Gln Asn Met Val Lys Lys Gly Ala Gly Phe Asn Trp Gly Ala Ala Gly
145                 150                 155                 160

Thr Ser Thr Ser Leu Trp Thr Gly Cys Met Leu Gly Asp Val Ile Gly
                165                 170                 175

Lys Ala Arg Pro Ser Lys Arg Ala Arg Phe Val Trp Met Glu Gly Ala
            180                 185                 190

Asp Asn Pro Ala Asn Gly Ala Tyr Arg Thr Cys Ile Arg Leu Ser Trp
        195                 200                 205

Cys Met Asp Pro Glu Arg Cys Ile Met Ile Ala Tyr Gln Gln Asn Gly
    210                 215                 220
```

-continued

```
Glu Trp Leu His Pro Asp His Gly Lys Pro Leu Arg Val Val Ile Pro
225                 230                 235                 240

Gly Val Ile Gly Gly Arg Ser Val Lys Trp Leu Lys Lys Leu Val Val
            245                 250                 255

Ser Asp Arg Pro Ser Glu Asn Trp Tyr His Tyr Phe Asp Asn Arg Val
        260                 265                 270

Leu Pro Thr Met Val Thr Pro Glu Met Ala Lys Ser Asp Asp Arg Trp
    275                 280                 285

Trp Lys Asp Glu Arg Tyr Ala Ile Tyr Asp Leu Asn Leu Gln Thr Ile
290                 295                 300

Ile Cys Lys Pro Glu Asn Gln Gln Val Ile Lys Ile Ser Glu Asp Glu
305                 310                 315                 320

Tyr Glu Ile Ala Gly Phe Gly Tyr Asn Gly Gly Val Arg Ile Gly
            325                 330                 335

Arg Ile Glu Val Ser Leu Asp Lys Gly Lys Ser Trp Lys Leu Ala Asp
            340                 345                 350

Ile Asp Tyr Pro Glu Asp Arg Tyr Arg Glu Ala Gly Tyr Phe Arg Leu
        355                 360                 365

Phe Gly Gly Leu Val Asn Val Cys Asp Arg Met Ser Cys Leu Cys Trp
370                 375                 380

Cys Phe Trp Lys Leu Lys Val Pro Leu Ser Glu Leu Ala Arg Ser Lys
385                 390                 395                 400

Asp Ile Leu Ile Arg Gly Met Asp Glu Arg Met Met Val Gln Pro Arg
            405                 410                 415

Thr Met Tyr Trp Asn Val Thr Ser Met Leu Asn Asn Trp Trp Tyr Arg
            420                 425                 430

Val Ala Ile Ile Arg Glu Gly Glu Ser Leu Arg Phe Glu His Pro Val
            435                 440                 445

Val Ala Asn Lys Pro Gly Gly Trp Met Asp Arg Val Lys Ala Glu Gly
    450                 455                 460

Gly Asp Ile Leu Glu Gln Lys Leu Ile Ser Glu Glu Asp Leu Asn Ser
465                 470                 475                 480

Ala Val Asp His His His His His His
            485
```

```
<210> SEQ ID NO 2
<211> LENGTH: 2070
<212> TYPE: DNA
<213> ORGANISM: Pichia angusta

<400> SEQUENCE: 2
atggattcta ttgtcactga ggtaacctat ggtctggaga tcaagaaaat caaagatatc      60
acggagctac cttttccagt caggcaagac tctcctctta ccgaggtgct tccaacagat     120
ctgaagacca agataatttt tgtcgctaga gatcctgacc ttcttagact cactggttca     180
cacccattca attctgagcc gccactgaca aagctttatg actcggggtt tctcactcca     240
gtgagtcttc actttgtgag aaaccacggc cccgttcctt acgttcctga tgaaaatatt     300
ttagactggg aagtttcaat tgaagggatg gttgaaacgc cttataaaat caaattgtca     360
gacataatgg agcagtttga tatctattca accccgtta ctatggtctg cgctggaaac     420
agaagaaagg agcagaatat ggtaagaag ggagccggtt caattgggg gcagctgga      480
acatctactt ctcttggac aggatgcatg cttggagatg taataggcaa ggctagacca     540
tcaaagagag caagattcgt atggatggag ggtgcagata atccggcaaa cggcgcatac     600
```

```
atggattcta ttgtcactga ggtaacctat ggtctggaga tcaagaaaat caaagatatc    660
acggagctac cttttccagt caggcaagac tctcctctta ccgaggtgct tccaacagat    720
ctgaagacca aagataattt tgtcgctaga gatcctgacc ttcttagact cactggttca    780
cacccattca attctgagcc gccactgaca aagctttatg actcggggtt tctcactcca    840
gtgagtcttc actttgtgag aaaccacggc cccgttcctt acgttcctga tgaaaatatt    900
ttagactggg aagtttcaat tgaagggatg gttgaaacgc cttataaaat caaattgtca    960
gacataatgg agcagtttga tatctattca accccgttca ctatggtctg cgctggaaac   1020
agaagaaagg agcagaatat ggtaaagaag ggagccggtt tcaattgggg agcagctgga   1080
acatctactt ctctttggac aggatgcatg cttggagatg taataggcaa ggctagacca   1140
tcaaagagag caagattcgt atggatggag ggtgcagata atccggcaaa cggcgcatac   1200
cgcacctgta tccgcttaag ctggtgtatg gaccctgaac ggtgcatcat gatcgcatac   1260
cagcagaacg gcgagtggtt gcatcctgac catggaaagc cccttcgagt agtaatcccc   1320
ggtgttattg gtggacgatc agtcaaatgg ctaaagaaac tagtagtgag cgatcggccg   1380
tctgaaaatt ggtatcatta ttttgataat cgggttcttc caaccatggt gacgccagag   1440
atggctaaaa gtgacgacag gtggtggaaa gacgagcgat atgccatata tgatctgaac   1500
ttgcaaacga tcatttgcaa gcccgaaaat cagcaggtta tcaagatttc agaggacgag   1560
tacgaaattg caggttttgg ctacaacgga ggtggagtca gaataggccg gattgaggtc   1620
agtcttgaca aagggaagag ttggaaactg gcagatatag actatccgga agacagatat   1680
agggaagcag gttacttcag attgtttggc ggacttgtga atgtttgcga cagaatgagc   1740
tgcctgtgct ggtgtttctg gaagctcaag gttcctcttt ctgaattagc aaggtcaaaa   1800
gatattctca ttcgtggcat ggatgagcgt atgatggttc agccgcgcac gatgtactgg   1860
aacgtaacgt ccatgctgaa caactggtgg tatcgagtcg ccattatccg cgagggtgag   1920
agtcttcgat ttgagcatcc cgtggtggcc aacaagcctg gcggttggat ggatagggtc   1980
aaggcagagg gtggagatat tctagaacaa aaactcatct cagaagagga tctgaatagc   2040
gccgtcgacc atcatcatca tcatcattga                                    2070
```